(12) United States Patent
Bergström

(10) Patent No.: US 6,478,042 B1
(45) Date of Patent: Nov. 12, 2002

(54) VALVE, ADAPTED TO CONNECT A FLOW MODULE TO A FLOW LINE

(75) Inventor: Jan Bergström, Bälinge (SE)

(73) Assignee: Amersham Pharmacia Biotech AB, Uppsala (SE)

( * ) Notice: Subject to any disclaimer, the term of this patent is extended or adjusted under 35 U.S.C. 154(b) by 0 days.

(21) Appl. No.: 09/194,479
(22) PCT Filed: May 12, 1997
(86) PCT No.: PCT/SE97/00770
§ 371 (c)(1),
(2), (4) Date: Dec. 4, 2000
(87) PCT Pub. No.: WO97/45661
PCT Pub. Date: Dec. 4, 1997

(30) Foreign Application Priority Data

May 23, 1996 (SE) .............................................. 9601958

(51) Int. Cl.⁷ .......................... F16K 3/314; B01D 15/08
(52) U.S. Cl. ...................................... 137/269; 137/627.5
(58) Field of Search ............................... 137/269, 627.5

(56) References Cited

U.S. PATENT DOCUMENTS

| 4,027,692 A | * | 6/1977 | Bouteille et al. ........ 137/269 X |
| 4,181,141 A | * | 1/1980 | Stoll et al. .............. 137/269 X |
| 5,766,460 A | * | 6/1998 | Bergstrom et al. ....... 210/198.2 |

* cited by examiner

Primary Examiner—Kevin Lee
(74) Attorney, Agent, or Firm—Royal N. Ronning, Jr.; Stephen G. Ryan

(57) ABSTRACT

A sliding valve having a flow line on which there may be placed a module having flow channel that can be connected and disconnected. The valve avoids the problem of liquid remaining in the flow channel of a first valve component by providing flow channel intersecting segment which intersects both components of the sliding valve so that in a module disconnecting orientation, each valve component defines separate segments of the flow channel while in the connected orientation, the valve components define a single flow channel. The construction allows for liquid flow through the valve independent of the module being in connected or disconnected position.

1 Claim, 5 Drawing Sheets

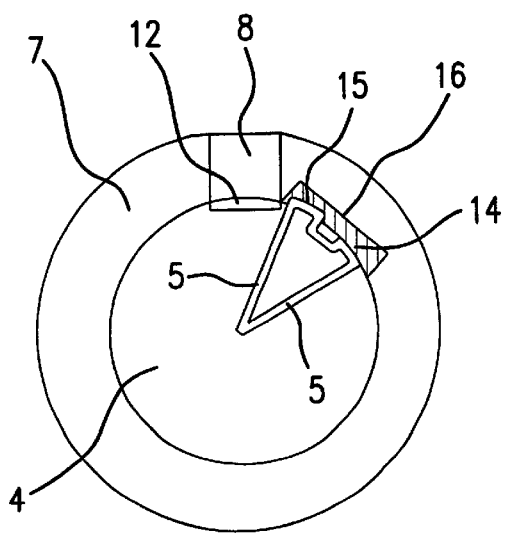
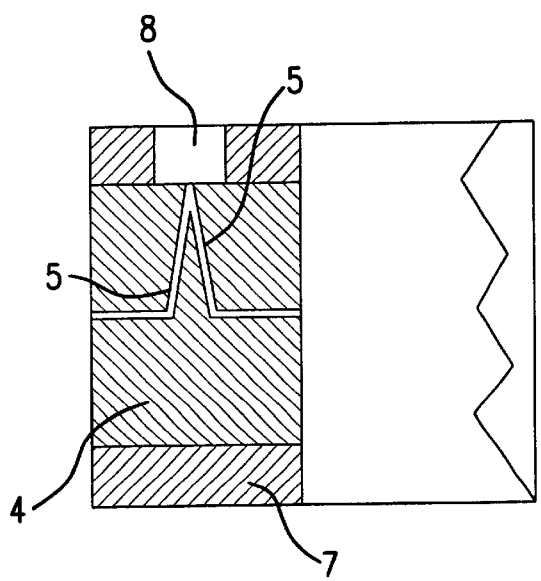
FIG.3a
FIG.3d
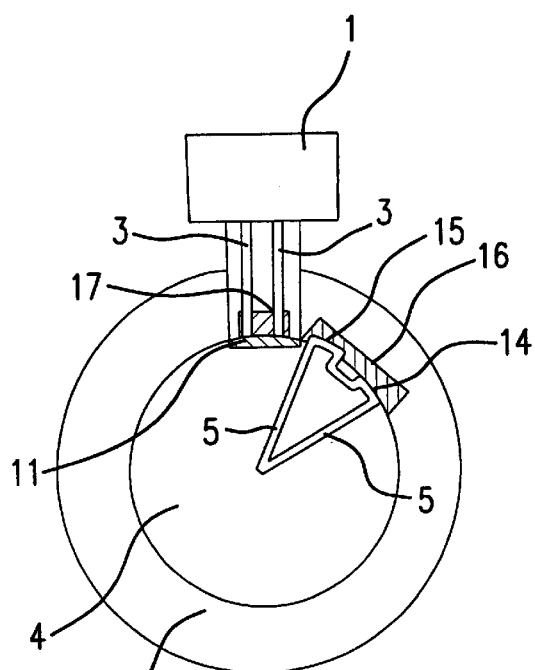
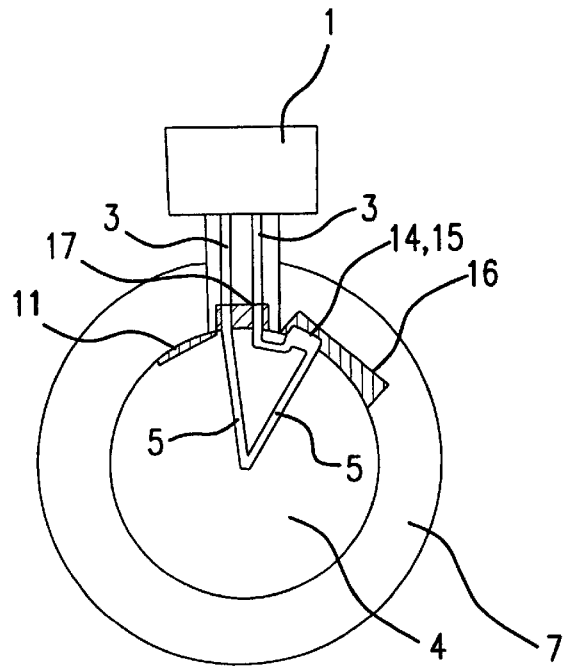
FIG.3b
FIG.3c

VALVE, ADAPTED TO CONNECT A FLOW MODULE TO A FLOW LINE

FIELD OF THE INVENTION

The invention relates to a valve adapted to connect a flow module to a flow line. Similar types of valves are previously disclosed in connection with chromatography systems (WO-A-9409879). The valve of the present invention is a modification of the type of valve operation exemplified by FIG. 4a of WO-A-9409879 (hereby incorporated by reference).

BACKGROUND OF THE INVENTION

Valves, operative to connect and dis-connect through displacement, are previously disclosed also in WO-A-8001507(Svensson), WO-A-8200698 (Svensson), EP-A-253,803 (Svensson,=U.S. Pat. No. 4,576,199), U.S. Pat. No. 2,634,750 (Raffa), U.S. Pat. No. 2,858,853 (Holl).

The invention comprises the type of valves which performs, similarly to the valve of FIG. 4 in WO-A-9409879 (see also FIG. 1 of the present disclosure) a sliding operation for connecting and dis-connecting a flow module (1) which allows a fluid flow there-through. Said module can be detachable (see FIG. 1 below and FIG. 4 of WO-A-9409879). The module can also be fixedly attached, i.e. constituting an integrated part of the valve. The flow module has inlet- and outlet openings (2i, 2u) resp., and a flow channel (3) disposed there-between.

A. a body I (4) with a flow channel (5) passing there-through and forming part of the flow line to which the flow module (1) is to be connected, the channel (5) being interrupted by openings (6u,6i) for connection to the inlet-and outlet openings (2i,2u) resp., of the flow module, and B. a body II (7), either incorporating or shaped to accommodate (8) the flow module, the body II slidably arranged on the body I (4), or vice versa, in such way that a. the flow module inlet and outlet 2i,2u), resp., sealingly connects to the openings (6u,6i) of the flow channel (5), when said bodies I and II are relatively displaced in the module connecting position, and b. the body II (7) admits liquid flow communication between openings (6u,6i) when said bodies I and II are relatively displaced in the module dis-connecting position.

When the flow module, according to WO-A-9409879, is in the module dis-connecting position, liquid flow communication between openings (6u, 6i) has been accomplished by means of the body II comprising a flow channel segment (9) with openings (10i, 10u) facing the body I and adapted to fit the flow channel openings (6u, 6i) of the body 1 (4). The openings (6u) and (6i), (2i) and (2u), and (10i) and (10u) are equally spaced. In WO-A-9409879, FIG. 4a shows a variant wherein the bodies I and II are linearly displaced relative to each other, so that connecting and dis-connecting of the module is effected according to FIG. 1 of the present disclosure. Arrangements, wherein the openings move accurately along the periphery of a circle (rotation) may likewise be contemplated for connecting and dis-connecting, resp.

The flow module of FIG. 1 may comprise a detachable sealing element (11) adapted to fit a recess (12) in the body I. As the body II, the flow module inserted therein, is displaced towards the right hand side of the figure, the sealing element (11) remains seated in the recess (12) so that the module openings (2i, 2u) are no longer covered but revealed to match the openings (6u, 6i) of the body I, in the module connecting position.

As used herein, the expression "flow module" refers to a module which allows for a flow to pass there-through, and which optionally displays a certain operative function. In the system disclosed by WO-A-9409879 such functions may be filtration, connection to external units, as injection port, sample loop, for detection, chromatography separation, etc.

Typically, valves of prior art have the disadvantage of liquid remaining in the channel (9) in the module connecting position. This is un-desired, since the remaining liquid may contaminate passing liquid and is liable to cause growth. Any remaining liquid usually calls for rinsing procedures.

BRIEF DESCRIPTION OF THE DRAWINGS

FIG. 1 shows a valve of prior art wherein connecting and disconnecting is accomplished by displacement. Sub

FIG. 3 shows an embodiment of the inventive valve wherein connecting/disconnecting is accomplished by the rotation of a cylinder, or by rotation of a sleeve surrounding the cylinder. Sub-FIGS. 3a, 3b and 3c are sectional views through the valve assembly, transversely to the longitudinal axis of the cylinder. Sub-FIG. 3d is a sectional view showing the flow line in the longitudinal direction of the cylinder.

DETAILED DESCRIPTION OF THE PREFERRED EMBODIMENT

Figure 1A:
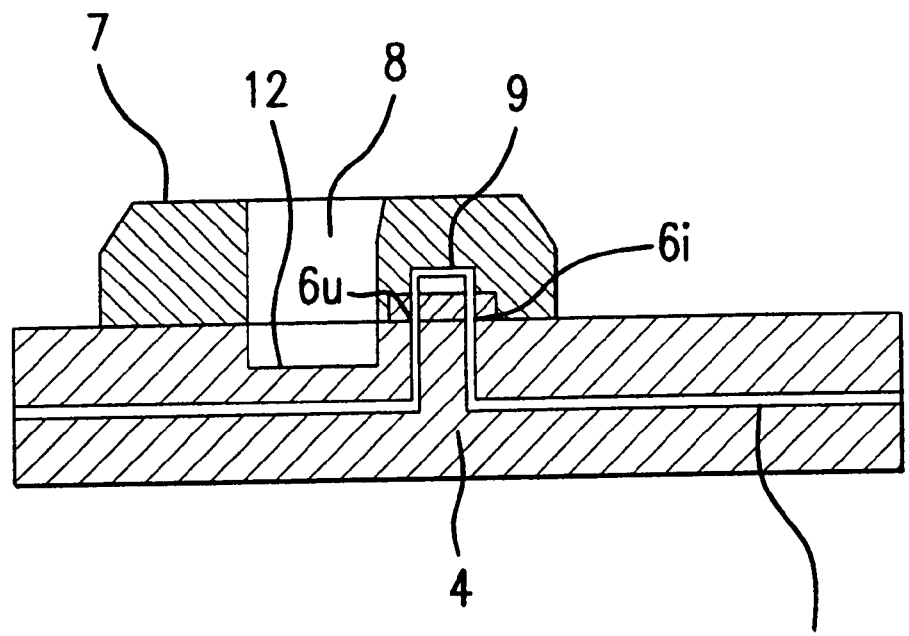
-FIGS. 1a and 1b show the valve in a dis-connecting position, without and with, resp., an inserted flow module. Sub
Figure 1B:
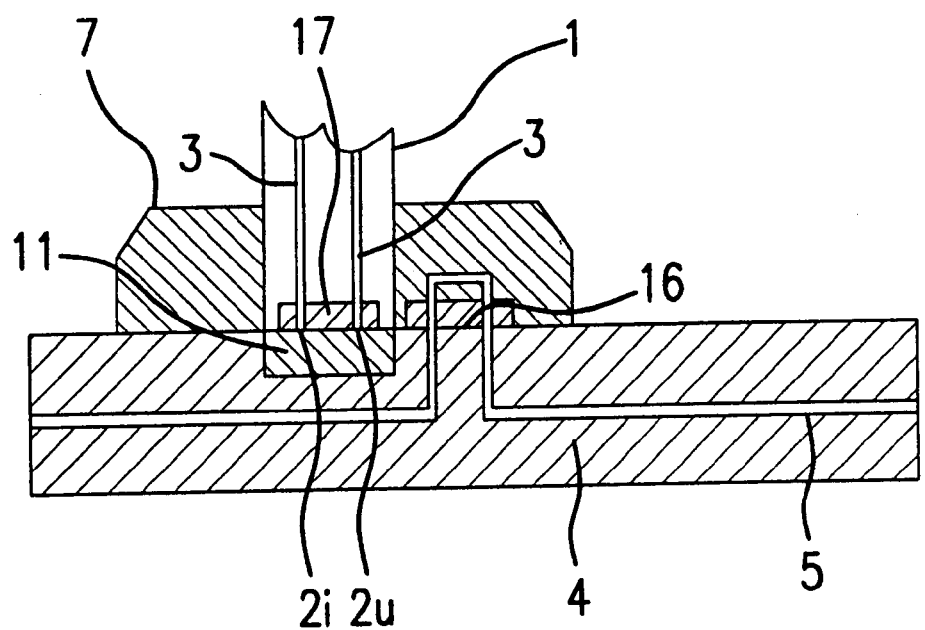
Figure 1C:
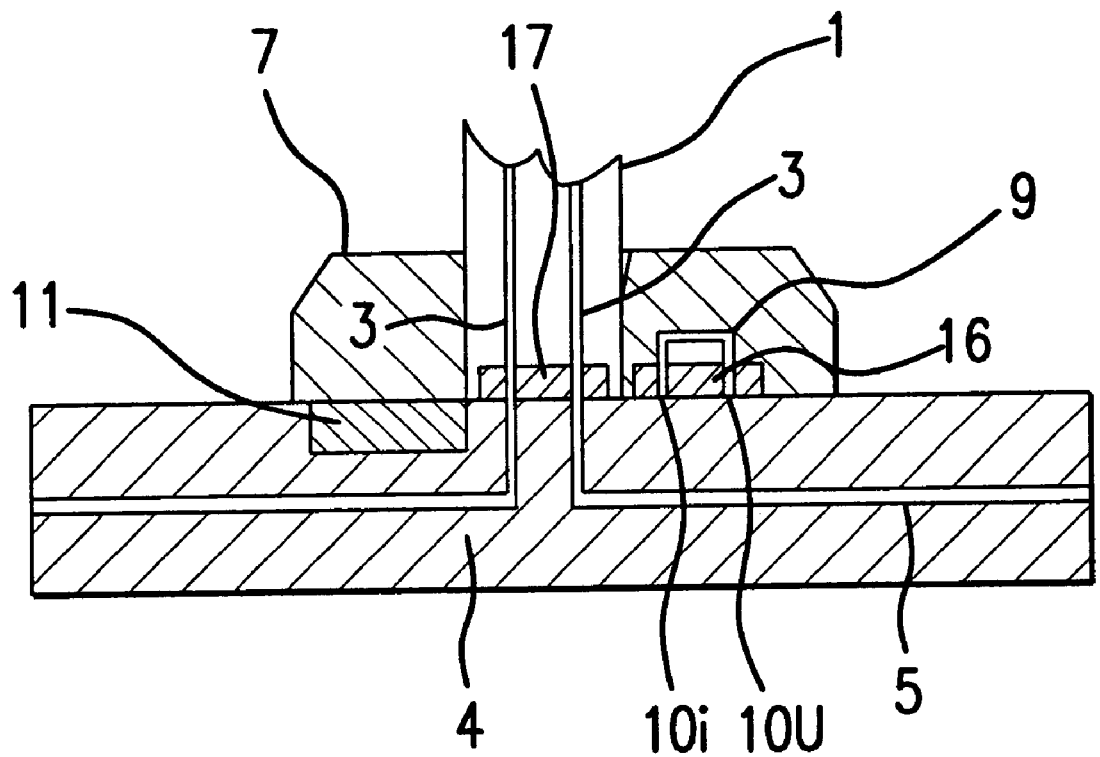
-FIG. 1c shows the valve with a flow module in connecting position. See FIG. 4a of WO-A-9409879.
Figure 2A:
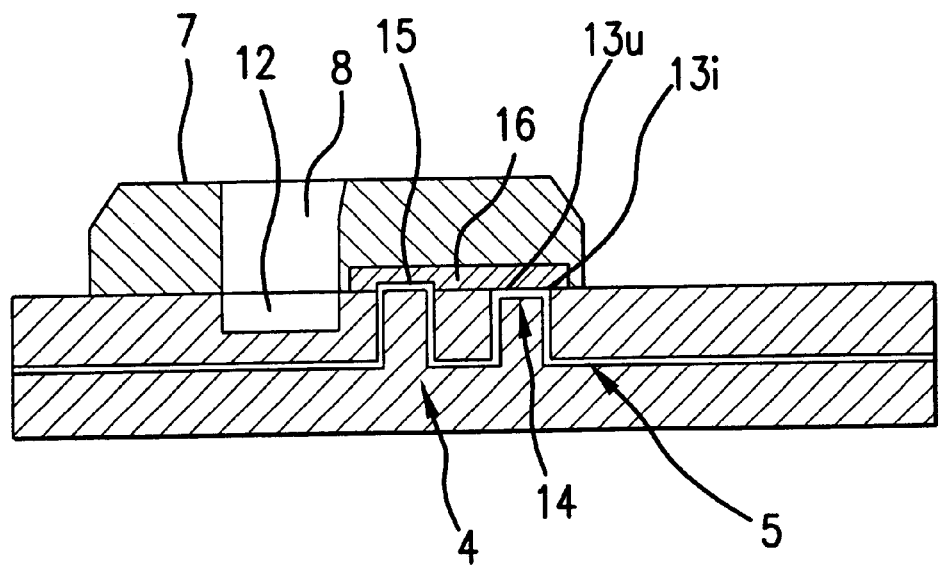
FIG. 2 shows the valve of FIG. 1 modified in accordance with the invention. Sub-FIGS. 2a, 2b and 2c corresponds to sub-FIGS. 1a, 1b and 1c, resp.
Figure 2B:
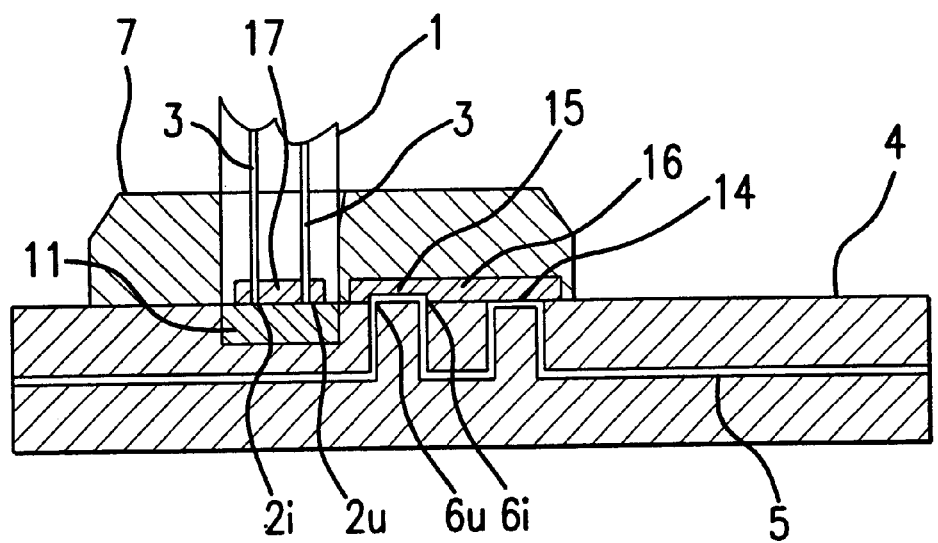
Figure 2C:
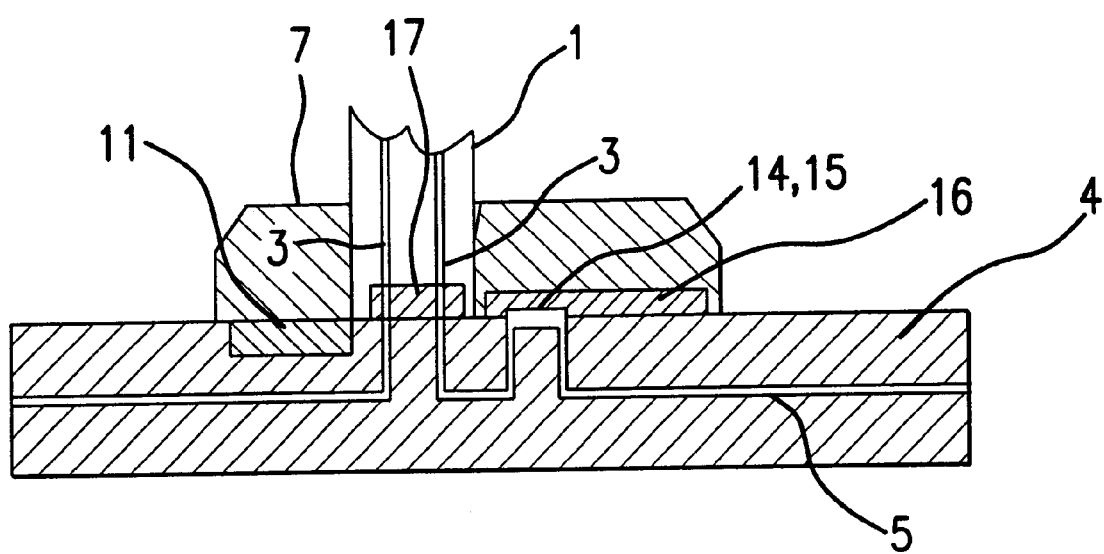

The present invention is disclosed with reference to FIGS. 2a–2c and FIGS. 3a–3d, and provides a solution to the abovesaid problem. FIGS. 2a–2c correspond to FIGS. 1a–1c. Elements of equivalent function are identically numbered. In the module connecting position, liquid flow communication between the openings (6u, 6i) is accomplished by means of:

1. the flow channel (5) of the body 1 (4) comprising an additional interruption with openings (13u, 13i), spaced equally as the openings (6u, 6i);

2. liquid flow communication between the openings (13u, 13i), in the module connecting position, is effected through a channel defined by a recess (14) which is formed in the body I(4) and extended between the openings (13u) and (13i), and a recess (15) formed in the body 11 (7) and extended between the openings (6u) and (6i).

In the module dis-connecting position, liquid flow communication between the openings (6u) and (6i) is effected through the recess (15) of the body II (7), and between the openings (13u) and (13i) through the recess (14) of the body I (4). The sectional areas of both recesses should be chosen not to cause any undesired interference with the flow. Normally, this means that the total sectional area of the two recesses substantially corresponds to the sectional area of the flow channel (usually within an allowable difference of +/−50%).

The inventive valve may be fixedly attached, as an integrated part of a liquid flow communication system. It may also be designed as a detachable part and connectable to a liquid flow communication system. One of the bodies I and II, or both, is movable relative the other body. The bodies I and II may be assembled from smaller units, e.g. in a way disclosed by WO-A-9409879. The flow module may be fixedly attached to the body II. As an alternative, it may be detachable and possible to replace in exchange for a flow module of different operative function, as in WO-A-9409879. The flow module has a flow channel (3), passing through a suitable function element, e.g. a separation medium for chromatography, a filter, etc. The module may also be adapted for connection to an external function. See WO-A-9409879 for further details. The flow module may comprise sealing elements (11) adapted to fit a recess in the body 1 (4) in accordance with FIG. 1. See also WO-A-9409879. Sealing elements (16',16",16'") are usually provided in combination with the pairs of openings (2i, 2u), (6u, 6i) and (13u, 13i), resp. The sealing elements are typically produced from a flexible, compressible material. In FIGS. 2a–2c, the sealing elements (16" and 16'") for the openings (6u, 6i) and (13u, 13i) are in form of a common sealing element.

In an alternative embodiment, connecting/dis-connecting is effected by relative rotation of the bodies, see e.g FIGS. 3a–3c. In this embodiment, the body I (4) is realized in the form of a cylinder-shaped body through which the flow channel (5) passes in longitudinal direction, preferably along the cylinder axis. The flow channel (5) is extended to openings (6u, 6i) and (13u, 13i) in the cylinder wall, wherein interconnecting recesses (15) and (14) are provided within the respective pair of openings. The body II (7), comprising an aperture (8) for accommodating a flow module (1), is supported on the cylinder wall in connection with the openings (6u, 6i) and (13u, 13i). The flow channel, which guarantees liquid flow in the module (1) connecting position, is defined by the recess (15) of the body II (7) and the recess (14) of body I (4). A sealing element is represented by reference numeral(16). Connecting and disconnecting the flow module (1) is accomplished by rotating the cylinder (the body I (4)) in relation to the body II (7), or vice versa. See FIGS. 3b–3c.

The invention is defined by the attached claim.

What is claimed is:

1. Valve for connecting a flow module to a flow line, said flow module having inlet and outlet openings and a flow channel disposed to admit a liquid flow there-between, the valve comprising
  a. a first body defining first and second openings and a flow channel passing there-through, the flow channel extending in fluid communication between the first and second openings, first and second openings being positionable in fluid communication with the inlet and outlet openings, respectively, of the flow module, and
  b. a second body, incorporating or adapted to accommodate the flow module, the first and second body being slidably arranged in such way that the module inlet and outlet openings sealingly connects in fluid communication with the first and second openings, respectively, when the first and second bodies are relatively displaced in a module connecting position, and the second body provides for liquid flow communication between openings when the first and second bodies are relatively displaced in a module dis-connecting position, wherein liquid flow communication between the first and second openings is accomplished in the module connecting position by means of:
  A. the flow channel of the first body further comprising an interruption with opposed openings equally spaced as the first and second openings, and
  B. liquid flow communication between the opposed openings, in the module connecting position, is effected through a channel defined by a first recess defined by the second body and extending in registerable fluid communication with the opposed openings, and by a second recess defined by the first body and extending in fluid communication with the opposed openings.

* * * * *